United States Patent [19]
Bishopric et al.

[11] Patent Number: 5,855,620
[45] Date of Patent: Jan. 5, 1999

[54] MATRIX SUBSTRATE FOR A VIABLE BODY TISSUE-DERIVED PROSTHESIS AND METHOD FOR MAKING THE SAME

[75] Inventors: Nanette H. Bishopric, Palo Alto; Linda Dousman, Boulder Creek; Yung-mae M. Yao, Menlo Park, all of Calif.

[73] Assignee: St. Jude Medical, Inc., St. Paul, Minn.

[21] Appl. No.: 741,086

[22] Filed: Oct. 30, 1996

Related U.S. Application Data

[62] Division of Ser. No. 424,218, Apr. 19, 1995, abandoned.

[51] Int. Cl.$^6$ .......................................................... A61F 2/02
[52] U.S. Cl. ............................... 623/11; 623/66; 128/893; 424/422; 424/423; 435/240.241; 435/240.243; 530/350; 530/356
[58] Field of Search ................................. 623/1, 2, 11, 12, 623/15, 16, 66; 424/422, 423; 435/240.241, 240.243; 530/350, 356; 128/898

[56] References Cited

U.S. PATENT DOCUMENTS

| | | |
|---|---|---|
| 3,318,774 | 5/1967 | Dingwall et al. . |
| 4,352,887 | 10/1982 | Reid et al. . |
| 4,539,716 | 9/1985 | Bell . |
| 4,553,974 | 11/1985 | Dewanjee . |
| 4,776,853 | 10/1988 | Klement et al. ........................ 8/94.11 |
| 4,801,299 | 1/1989 | Brendel et al. .............................. 623/1 |
| 4,976,733 | 12/1990 | Girardot . |
| 5,192,312 | 3/1993 | Orton .......................................... 623/2 |
| 5,336,616 | 8/1994 | Livesey et al. ...................... 435/240.2 |
| 5,397,353 | 3/1995 | Oliver et al. .............................. 623/11 |
| 5,558,875 | 9/1996 | Wang ...................................... 424/422 |
| 5,613,982 | 3/1997 | Goldstein ................................. 623/11 |

FOREIGN PATENT DOCUMENTS

| | | |
|---|---|---|
| WO 9603093A1 | 2/1996 | WIPO . |

OTHER PUBLICATIONS

Anderson, et al. *In Vitro Endothelialization of Small–Caliber Vascular Grafts*, Surgery, pp. 577–586 (1987).

Bengtsson, et al., *Lining of Viable and Nonviable Allogeneic and Xenogeneic Cardiovascular Tissue With Adult Human Venous Endothelium*, J. Thoracic & Cardiovas. Surg., vol. 106, No. 3, pp. 434–443 (1993).

Eybl, et al., *Endothelial Cell Lining of Bioprosthetic Heart Valve Materials*, J. Thoracic & Cardiovas. Surg., vol. 104, No. 3, pp. 763–769 (1992).

Herring, et al., *A Single–Staged Technique for Seeding Vascular Grafts With Autogenous Endothelium*, Surgery, pp. 498–504 (1978).

Ishihara, et al., *Occurrence and Significance of Endothelial Cells in Implanted Porcine Bioprosthetic Valves*, The American Journal of Cardiology, vol. 48, pp. 443–454 (1981).

Loose, et al., *Preparing Heart Valve Allografts for Endothelial Cell Seeding*, Transplantation Proceedings, vol. 25, No. 8, pp. 3244–3246 (1993).

Lupinetti, et al., *Endothelial Cell Replication in an In Vivo Model of Aortic Allografts*, Ann. Thorac. Surg., vol. 56, pp. 237–241 (1993).

(List continued on next page.)

*Primary Examiner*—John G. Weiss
*Assistant Examiner*—Francis K. Cuddihy
*Attorney, Agent, or Firm*—Hallie A. Finucane; Fish & Richardson P.C., P.A.

[57] ABSTRACT

Disclosed is a process for treating body tissues such as vascular structures to remove barriers to recellularization before and after implantation in a human host. The body tissue, for example a heart valve, is subjected to a hypotonic/hypertonic treatment, then treated with enzymes to provide a collagen- and elastin-containing matrix suitable for recellularization.

10 Claims, 4 Drawing Sheets

OTHER PUBLICATIONS

Moritz, et al., *Improved Endothelialization of Postfixation Treated Biological Vascular Grafts*, The Intl'l Journal of Artificial Organs, vol. 15, No. 5, pp. 289–294 (1992).

Zilla, et al., *Clinical In Vito Endothelialization of Femoropopliteal Bypass Grafts: An Actuarial Follow–Up Over Three Years*, J. Vasc. Surg., vol. 19, No. 3, pp. 540–548 (1994).

Lefevre et al., *New Artificial Connective Matrix–Like Structure Made of Elastin Solubilized Peptides and Collagens: Elaboration, Biochemical and Structural Properties*, Biomaterials vol. 13, No. 1, pp. 28–33 (1992).

Webster et al., *Induction and Nuclear Accumulation of Fos and Jun Proto–oncogenes in Hypoxic Cardiac Myocytes*, The Journal of Biological Chemistry, vol. 268, No. 22, Issue of Aug. 5, pp. 16852–16858 (1993).

MATRIX SUBSTRATE FOR A VIABLE BODY TISSUE-DERIVED PROSTHESIS AND METHOD FOR MAKING THE SAME

This is a division of application Ser. No. 08/424,218 filed Apr. 19, 1995 now abandoned.

FIELD OF THE INVENTION

This invention relates to a process for treating body tissues such as vascular structures to remove barriers to recellularization by autologous or allogeneic cells before and after implantation in a human host. More particularly, the invention relates to enzyme-based removal of antigen-bearing cell membranes and other cell remnants from body tissues such as aortic heart valves. This provides a potentially non-antigenic collagen- and elastin-containing matrix with reduced calcification potential and improved capacity for recellularization.

BACKGROUND OF THE INVENTION

Currently available prostheses for the replacement of defective heart valves and other vascular structures may be classified as mechanical or bioprosthetic. Mechanical structures such as heart valves are manufactured from biocompatible metals and other materials such as Silastic®, graphite, titanium, and Dacron®. Although mechanical valves have the advantage of proven durability in decades of use, they frequently are associated with a high incidence of blood clotting on or around the valve. This can lead to acute or subacute closure. For this reason, patients with implanted mechanical valves generally must remain on anticoagulants for as long as the valve remains implanted. Anticoagulants are inconvenient to take and impart a 3–5% annual risk of significant bleeding.

Bioprosthetic valves were introduced in the early 1960's and are typically derived from pig aortic valves or are manufactured from other biological materials such as bovine pericardium. Xenograft heart valves invariably are tanned in glutaraldehyde prior to implantation. A major rationale for the use of autologous or heterologous biological material for heart valves is that the profile and surface characteristics of this material are optimal for laminar, nonturbulent blood flow. The result is that intravascular clotting is less likely to occur than with mechanical valves. This concept has been proven in clinical use with the well-documented reduced thrombogenicity of current versions of glutaraldehyde-fixed bioprosthetic valves.

Unfortunately all such valves are limited by the tendency to fail, often catastrophically, beginning about 7 years after implantation. Few bioprosthetic valves remain functional after 12 years. Valve degeneration is particularly rapid in the young and during pregnancy. Replacement of a degenerating valve prosthesis is particularly hazardous in the elderly and in situations of emergency replacement. As a consequence, there are few real indications and many contraindications to the use of bioprosthetic valves.

Clearly, solving the problem of bioprosthetic valve degeneration would be highly desirable. Calcification appears to be the primary insult leading to degeneration. Efforts to address the calcification problem have included treating glutaraldehyde-fixed valves with compounds such as toluidine blue, sodium dodecyl sulfate and diphosphonate to reduce calcium nucleation. However, these efforts have been unsuccessful in vivo. Other approaches include removal of reactive glutaraldehyde moieties from the tissue by a chemical process. Still other approaches have included development of alternate fixation techniques, since evidence suggests that the fixation process itself contributes to calcification and mechanical deterioration. Finally, since nonviable cells present in transplanted tissue are sites for calcium deposition, various processes have been developed to remove cells from the valve matrix prior to implantation. Most of these processes appear to reduce calcification in animal models in short-term use, but clinical data are not yet available.

Another major disadvantage to bioprosthetic devices is the failure of such devices to be self-maintaining. Neither cadaveric allografts nor glutaraldehyde-fixed xenografts have significant populations of viable cells, and glutaraldehyde is highly cytotoxic. Since viable cells in the valve provide protection against the insudation of calcium, it is likely that any devitalized bioprosthesis will undergo calcification over time. Hence it is essential to the development of a durable prosthetic device that it support ingrowth and colonization of cells 1) from the host during the period after implantation, 2) from autologous or allogeneic sources before implantation, e.g., during a period of in vitro culture prior to implantation, or 3) from both the host after implantation and from various sources prior to implantation.

Various detergents and nucleases have been used in the past to obtain extracellular matrix from body sources for use as potential graft materials. Detergent treatment of a glutaraldehyde-fixed body structure is disclosed in U.S. Pat. No. 4,323,358 as a method for retarding mineralization after implantation. Decellularization of unfixed, untreated body structures by detergent methods is disclosed in U.S. Pat. No. 4,352,887 as a means for producing a substrate for cell culture, and in U.S. Pat. No. 4,801,299 as a means for producing sterile body implants. U.S. Pat. No. 4,776,853 discloses a specific process for achieving decellularization by a combination of nonionic and anionic detergents, deoxyribonuclease (DNAse) and ribonuclease (RNAse).

The field of tissue and organ transplantation is growing rapidly as a result of a number of advances in the areas of organ preservation, surgical techniques, and immunosuppressive agents. As a result, shortages of implantable material are often the major obstacle in the use of bioprosthetic implants. As used herein, the term "autologous" refers to cells, tissues or other biological structures derived from the same individual designated to receive the implant. The term "allogeneic" refers to cells, tissues or other biological structures taken from other members of the same species. The term "xenogeneic" refers to cells, tissues or other biological structures taken from a member of a species other than the species of the individual receiving the implant.

Shortages of implantable materials for human patients are particularly acute for heart valves, where autologous structures such as the pulmonic valve can only infrequently be used as a source of replacement material, and allogeneic implantable materials are limited. Improved methods of cryopreservation have increased the number of available allogeneic bioprosthetic implants. Extending the use of cryopreservation to xenogeneic body sources is disclosed in U.S. Pat. No. 5,336,616. That patent describes a method for processing and preserving acellular collagen-based tissue matrix for transplantation that includes a detergent-based decellularization step. Decellularization is followed by cryopreservation and dehydration. On rehydration, the tissue is inoculated with viable autologous or allogeneic cells.

A number of specific conditions that affect use of xenogeneic material for heart valve implantation have yet to be fully addressed. These include the exacting requirements for mechanical integrity in short- and long-term use, as unscheduled replacement of these structures is difficult and risky. Long-term durability is affected not only by the harvesting and decellularization processes, but by the ability of cells to enter and carry out maintenance functions in the implanted tissue. That viable cells are an essential determinant of valve survival is clear from longitudinal studies in allograft recipients. In these studies, proper allograft preservation can maximize the number of viable cells remaining in the tissue as determined by matrix protein synthesis. Preservation techniques that do not promote cell survival, such as long term storage at 4° C., are associated with reduced in vivo durability and increased reoperation rates.

The repopulation of matrix by contiguous cells in the host, or by inoculated autologous or allogeneic cells in tissue culture, can be critical to development of a successful implant. In turn, the characteristics of the matrix can be critical to the repopulation ("recellularization") process. For example, failure to effectively reduce the dense cellularity of the donor aortic root is likely to be a significant obstacle to cell ingrowth, due to the physical barrier created by the cellular architecture of the root, or to the effect of contact inhibition between in-migrating host cells and the remaining in situ donor cells.

Previously described processing methods have been developed and tested with the goals of reducing antigenicity and mineralization of the xenograft, but have dealt only incidentally with the problem of recellularization. Thus, the adequacy of decellularization and the ability of the decellularized matrix to support ingrowth by autologous or allogeneic cells remains to be demonstrated. Moreover, the physical constraints imposed by the method of implantation have not been considered in envisioning how host cells may migrate into and repopulate a decellularized matrix following implantation. For example, methods of implantation may include use of a Dacron® sewing ring in the case of xenograft heart valves, or freehand attachment via the root structure in the case of allogeneic heart valves. Each of these methods presents distinctive challenges for obtaining adequate recellularization of the decellularized matrix. The methods disclosed herein provide a useful substrate for ingrowth by host cells following implantation due to enhanced removal of cells from the host/graft interface.

SUMMARY OF THE INVENTION

The invention includes a method of decellularizing a body tissue to form an extracellular matrix having substantially intact collagen and elastin components, where the matrix is capable of being recellularized in vitro or in vivo. The method comprises subjecting the body tissue to a hypotonic/hypertonic treatment, then treating the body tissue with an enzyme-based solution comprising lipase and deoxyribonuclease. The hypotonic/hypertonic treatment may comprise sequential incubation of the body tissue in a hypotonic solution and then in a hypertonic solution; alternatively, the hypotonic/hypertonic treatment may comprise sequential incubation of the body tissue in a hypertonic solution and then in a hypotonic solution.

The body tissue may comprise vascular tissue, for example a heart valve. The enzyme-based solution may include a protease in addition to the lipase and deoxyribonuclease. The protease may comprise trypsin and the lipase may comprise phospholipase, for example one or more phospholipases selected from the group consisting of phospholipase $A_2$, phospholipase C, and phospholipase D. The enzyme-based solution may further comprise ribonuclease.

After the enzyme-treatment described above, the body tissue can be washed in a buffered salt solution lacking calcium and magnesium and containing a chelating ligand and then stored in a buffered salt solution that lacks calcium, magnesium and a chelating ligand. These buffered salt solutions, as well as the solutions used for the hypotonic/hypertonic treatment, may include an antioxidant and a protease inhibitor.

The invention also includes a method for recellularizing a bioprosthetic implant, comprising contacting an extracellular matrix, prepared as described above, with cells, and maintaining the cells and the extracellular matrix together in vitro.

The invention further includes a bioprosthetic implant comprising an extracellular matrix having substantially intact collagen and elastin components. The matrix is formed by subjecting a body tissue to a hypotonic/hypertonic treatment as described above, then treating the body tissue with an enzyme-based solution comprising lipase and deoxyribonuclease.

The body tissue used to form the extracellular matrix of the bioprosthetic implant may comprise vascular tissue, for example a heart valve. The enzyme-based solution may include a protease in addition to the lipase and deoxyribonuclease. The protease may comprise trypsin and the lipase may comprise phospholipase, for example one or more phospholipases selected from the group consisting of phospholipase $A_2$, phospholipase C, and phospholipase D. The enzyme-based solution may further comprise ribonuclease.

After the enzyme-treatment described above, the body tissue can be washed in a buffered salt solution lacking calcium and magnesium and containing a chelating ligand and then stored in a buffered salt solution that lacks calcium, magnesium and a chelating ligand. These buffered salt solutions, as well as the solutions used for the hypotonic/hypertonic treatment, may include an antioxidant and a protease inhibitor.

The invention further comprises a bioprosthetic implant comprising an extracellular matrix that includes living cells. To form such a recellularized bioprosthetic implant, cells are added to the matrix following the above-described enzyme treatment, for example by combining the cells with the extracellular matrix in vitro.

In situations where the body tissue is a heart valve including a root and/or ascending aortic wall, the present invention provides that the root and ascending aortic wall are operatively decellularized following the enzyme treatment. That is, the ascending aortic wall and root are sufficiently decellularized so as to permit useful recellularization in vitro or in vivo.

DETAILED DESCRIPTION OF THE INVENTION

The present invention covers a process that thoroughly removes intact cells from body tissues such as vascular structures including the porcine heart valve and root structure. The process includes use of an enzyme-based solution having proteolytic and lipolytic action, leaving collagen and elastin fibers substantially intact. The process of the invention results in enhanced removal of cells from vascular structures, in particular the densely fibrous annulus of the aortic root of a heart valve. This allows for the in-migration of cells, for example host cells in contact with the outer surface of an implanted heart valve. The methods of the present invention provide for superior decellularization in the important zone at the base of the leaflet, where the aortic root is thickest, while preserving elastin and collagen.

Figure 2:
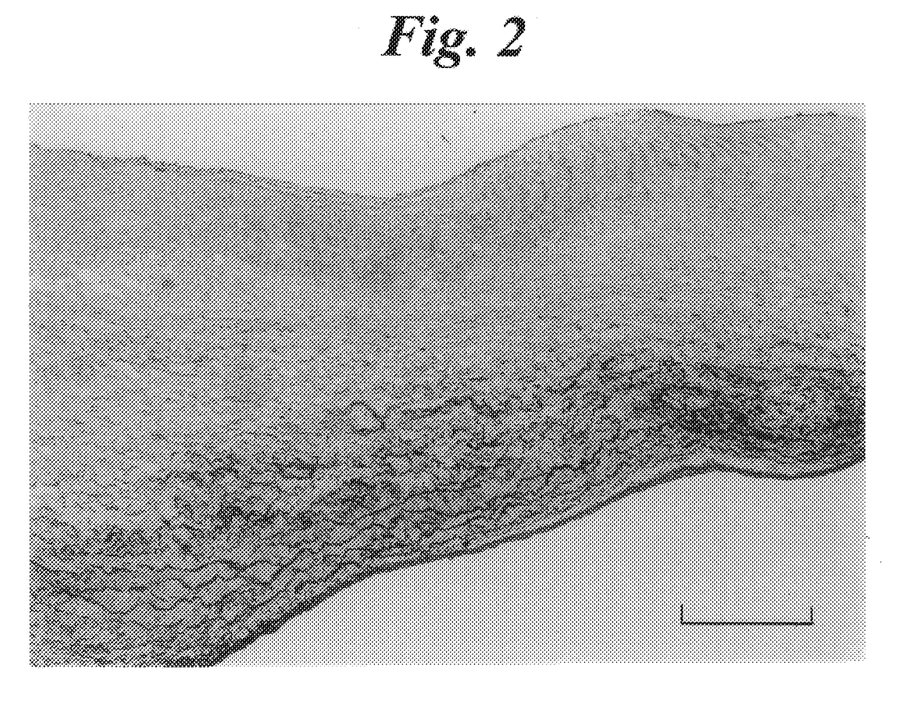
FIG. 2 is a light micrograph of a porcine aortic valve leaflet decellularized with a phospholipase-based process of the present invention (see Example 2, below). Bar=200 μm.
Figure 3:
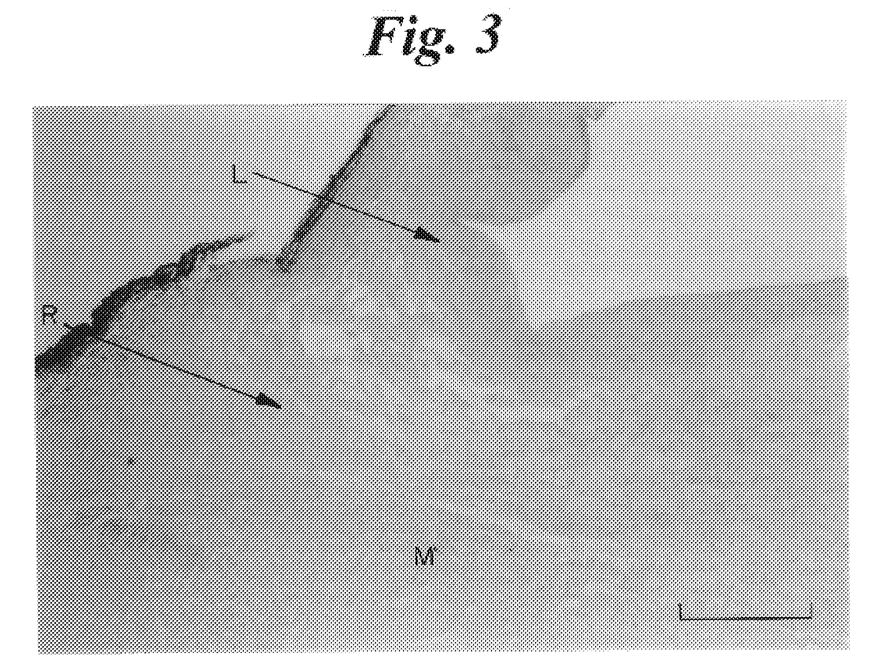
FIG. 3 is a light micrograph of a porcine aortic valve leaflet at its insertion into the aortic wall, decellularized by the process of Example 2, below. Bar=400 μm.

Studies utilizing light and transmission electron microscopy reveal that the process results in effective removal of intact cells (see Examples 1 and 2 and FIGS. 2 and 3). Biochemical assays demonstrate extraction of approximately 90% of potentially antigenic cytoplasmic and soluble protein components (see Example 1, below). A matrix prepared using the methods of the present invention provides a suitable substrate for attachment of both fibroblast and endothelial cells.

In some cases, it may be desirable to store the intact vascular structure prior to the decellularization process. This is particularly true since organ procurement may not coincide with optimal timing for decellularization. It is important to be able to store freshly harvested material that has not been subjected to extended periods of warm or cold ischemia as the latter may result in the leakage of destructive enzymes and chemicals from dying cells in the tissue and subsequent compromise of mechanical integrity. It is likely that procurement issues account for a significant part of the known variability in the quality of implanted xenograft material. Consequently, the freshly harvested tissue is incubated in a cryopreservation solution if it is not to be decellularized immediately. This cryoprotectant solution contains one or more physiologic buffers including but not limited to HEPES and bicarbonate, amino acids, non-penetrating cryoprotectant serum components, pH indicator dye and a cell penetrating cryoprotectant, preferably dimethylsulfoxide. This process does not appear to significantly alter the collagen or elastin matrix as determined by histological assessment.

Glutaraldehyde is widely used as a processing step in the preparation and preservation of xenograft heart valves and other implant materials, as it provides antigenic masking as well as sterilization. However, this treatment impairs the mechanical properties of the valve and may contribute to mineralization of the tissue after implantation. As an alternative to glutaraldehyde treatment for sterilizing the tissue after decellularization, the matrix may be given a post-processing exposure to gamma or other irradiation sources. A dose of 25 Kgray has been determined to be sufficient for sterilization without apparent compromise of the integrity of the native collagen/elastin matrix. Sterilization by this means allows the decellularized matrix to be placed in tissue culture with or without antibiotics to allow attachment of desired allogeneic or autologous cellular components. Such a matrix can be readily colonized by both fibroblasts and endothelial cells as well as other cell types.

The invention can be used to prepare a prosthetic implant for use in human patients. In particular, patients with symptoms of acute or chronic vascular insufficiency or stenosis resulting from congenital or acquired valve defects, infection, degeneration, or failure of a previously implanted vascular prosthesis can be provided implants prepared by the methods of the present invention. The invention is illustrated with respect to preparation of porcine heart valves, although it will be apparent to the ordinary skilled artisan that the methods of the present invention are generally applicable to a body tissue having an extracellular matrix of collagen and elastin that is colonized with living cells.

In one embodiment, porcine heart valves or other vascular structures are obtained immediately after slaughter from an abattoir. Intervals of 4–6 hours after slaughter are optimal but this period may be extended up to about 48 hours with refrigeration to 4° C. If valves are to be harvested, they are trimmed from the heart. The valve or other vascular structure preferably is washed in ice-cold normal saline and transferred to a decellularization solution for further processing. Alternatively, after a 30-minute incubation in a cryoprotectant solution, the tissue is frozen at −20° C. and stored until needed.

The tissue then may be placed in a series of decellularization solutions including:

A. A hypotonic solution comprising a buffer, a chelating ligand, antibiotics such as anti-bacterial and/or antifungal agents, a protease inhibitor and an antioxidant. Preferably the buffer is 10 mM Tris HCL, pH 8.0±0.5. The chelating ligand may be any ion chelator that functions to provide generalized enzyme inhibition. Preferably the chelating ligand is 5mM ethylenediaminetetraacetic acid (EDTA). Antibiotics may include, without limitation, one or more of neomycin, streptomycin, penicillin, gentamicin, and Amphotericin B. Protease inhibitors may include, without limitation, one or more of aprotinin, leupeptin and phenylmethylsulfonyfluoride (PMSF). Preferably the protease inhibitor is PMSF. The antioxidant may be any molecule having significant antioxidant activity, including but not limited to butylated hydroxyanisole (BHA), butylated hydroxytoluene (BHT), glutathione, α-tocopherol and ascorbate. Preferably the antioxidant is BHA at a concentration of 0.1 mM.

B. A hypertonic saline solution preferably containing a buffer, a chelating ligand, antibiotics, protease inhibitors and antioxidant as above. Preferably the hypertonic saline solution contains 1M NaCl, with 10 mM EDTA as chelating ligand. The purpose of the hypertonic treatment is to assist in the disruption of cells and to loosen cell-matrix attachments throughout the tissue.

NOTE: Incubation in solutions A and B above constitutes a hypotonic/hypertonic treatment of the body tissue. The treatment of a selected body tissue such as a vascular structure with a hypotonic solution and a hypertonic solution assists in cell rupture and facilitates subsequent enzyme digestion and dissolution of cell membranes and intracellular materials. As used herein, the term "hypotonic/hypertonic treatment" includes incubation in a hypotonic solution followed by incubation in a hypertonic solution or, alternatively, incubation in a hypertonic solution followed by incubation in a hypotonic solution.

C. A wash solution comprising a buffered physiological salt solution, pH 7.4±0.2, supplemented with calcium and magnesium. Preferably the buffer is a biological buffer such as N-[2-Hydroxyethyl]piperazine-N'-[2-ethanesulfonic acid] (HEPES). Preferably the calcium is 1 mM calcium, the magnesium is 1 mM magnesium. The wash solution may contain antibiotics if necessary to maintain sterility. Antibiotics may include, without limitation, neomycin, streptomycin, penicillin, gentamicin, and Amphotericin B.

D. An enzyme-based solution containing protease, lipase deoxyribonuclease and further containing antibiotics. Preferably the protease is trypsin. Preferably the lipase comprises a plurality of phospholipases, each of which attacks a different type of lipid bond in the biological cell membrane. Most preferably the lipase comprises one or more of the following: phospholipase $A_2$, phospholipase C and phospholipase D. The deoxyribonuclease may be, for example, deoxyribonuclease I (DNAse I). Ribonuclease, for example RNase A, may be included in the enzyme-based solution with deoxyribonuclease to facilitate digestion of nucleic acids. Antibiotics may include, without limitation, neomycin, streptomycin, penicillin, gentamicin, and Amphotericin B.

In an alternative embodiment, protease (e.g., trypsin) may be omitted from the enzyme-based solution.

E. A wash solution consisting of a buffered physiological salt solution without calcium or magnesium, and further containing a chelating ligand, an antioxidant, and a protease inhibitor. Preferably the buffer is 10 mM HEPES, the chelating ligand is 10 mM EDTA, the antioxidant is 0.2 mM BHA and the protease inhibitor is 1 μM PMSF. The wash solution may contain antibiotics if necessary to maintain sterility. Antibiotics may include, without limitation, neomycin, streptomycin, penicillin, gentamicin, and Amphotericin B.

F. A storage solution as in "E." above, but omitting a chelating ligand, and supplemented with active concentrations of antibiotics. Antibiotics may include, without limitation, neomycin, streptomycin, penicillin, gentamicin, and Amphotericin B.

In an alternative embodiment, structures prepared according to the methods of steps A–F above may be sequentially processed through steps B–E a second time.

In an alternative embodiment, structures prepared according to the methods of steps A–F above may be sterilized prior to implantation. In a further alternative embodiment, the structures prepared as in steps A–F above may be removed from the storage solution and fixed in glutaraldehyde for implantation. In a still further embodiment, the structures prepared as described in steps A–F above may be inoculated with allogeneic or autologous cells in vitro prior to implantation. Cell types used for in vitro inoculation can include, without limitation, dermal fibroblasts, cardiac fibroblasts, myofibroblasts, smooth muscle cells, and autologous endothelial cells and fibroblasts derived from host tissues including fat and peripheral vein.

The present invention provides a method for preparing a decellularized tissue implant, such as a heart valve, which allows for the reintroduction of viable cells either by ingrowth from the host or by pre-colonizing with cell lines derived for this purpose from the host or from immunotolerable sources such as human dermal fibroblasts. The invention provides a novel enzyme-based protocol that provides high selectivity of action on cell membranes and membrane matrix attachment, leaving a substantially intact collagen- and elastin-containing substrate as determined by histological assessment as shown in FIGS. 2 and 3.

As applied to heart valves, the present invention, unlike existing detergent-based processes, removes cells not only in the leaflet but also in the root and adjacent aortic wall which is to be directly apposed to the host valve structure during surgical implantation. Barriers to the ingress of host cells are removed, facilitating the critically important long-term remodeling process. Moreover, the invention results in a collagen- and elastin-containing matrix that can be colonized in vitro by endothelial, fibroblast or other cell types prior to implantation.

The invention will be further understood with reference to the following illustrative embodiments, which are purely exemplary, and should not be taken as limiting the true scope of the present invention as described in the claims.

EXAMPLE 1

Phospholipase Plus Protease Protocol

At the slaughterhouse, adult pigs were sacrificed and the hearts immediately removed and stored on ice until ready for use (about 4–8 hr later). In all of the EXAMPLES disclosed herein, aseptic techniques, laminar flow hoods for tissue and cell culture, and sterile solutions and containers were used to prepare the sterile cell-free tissue. Sources of reagents given below were used throughout the Examples. Procedures were as follows:

1. The aortic valve was removed from each heart and rinsed extensively in isotonic saline (0.9% NaCl in deionized, distilled water) supplemented with a 100 U/ml penicillin–100 μg/ml streptomycin solution (Gibco BRL, hereinafter Gibco, 15140-031 or equivalent) and 1 μM PMSF (Sigma P-7626 or equivalent). When used, PMSF was added to solutions just prior to use due to its limited duration of activity.

2. The valves were transferred to a 1.0 liter, sterile, screw capped container and incubated in a hypotonic solution consisting of 10 mM TRIS pH 8.0 (Ultra Pure, ACS grade, for cell culture, Gibco 11310-026 or equivalent), 5 mM EDTA (Sigma E-6511 or equivalent), supplemented with a 100 U/ml penicillin–100 μg/ml streptomycin solution, 0.1 mM BHA (Sigma B-1253 or equivalent) and 1 μM PMSF. The incubation period was 22 hours, at 4° C., on a shaking platform, 110 rpm. Three to six valves were incubated in 90 ml/valve of the solution (270–540 ml total). The spent solution was exchanged for fresh solution two times during the incubation period, for a total of three volume changes.

3. At the end of the incubation period the solution was decanted and replaced with a hypertonic solution consisting of 50 mM TRIS, 10 mM EDTA, 1.0N NaCl, pH 8.0, supplemented with a 100 U/ml penicillin–100 μg/ml streptomycin solution, 0.1 mM BHA and 1 μM PMSF. The valves were incubated in this solution for 22 hours, at 4° C., on a shaking platform, 110 rpm. The spent solution was exchanged for fresh solution two times during the incubation period, for a total of three volume changes 4. The valves were transferred to sterile 1.0 liter capped containers containing about 500 ml Hank's balanced salt solution (HBSS), with 1 mM $Ca^{2+}$, 1 mM $Mg^{2+}$, and 10 mM HEPES, pH 7.4 (Sigma H-3375 or equivalent). The valves were washed for 15 min at room temperature, on a shaking platform, 110 rpm. The spent solution was decanted and fresh solution was added to the containers and the washing procedure was repeated for a total of three washes. The tissue was then incubated in fresh solution for 30 min, at 37° C., with agitation on a shaking platform, 110 rpm.

5. The valves were transferred to a smaller, sterile, capped vessel containing a solution consisting of phospholipase $A_2$ (5 U/ml) (Sigma P-9279 or equivalent), phospholipase C (2.5 U/ml) (Sigma P-7633 or equivalent), phospholipase D (10 U/ml) (Sigma P-8023 or equivalent), DNase I (50 μg/ml) (Sigma D-5025 or equivalent), RNase A (83.3 μg/ml) (Sigma R-5125 or equivalent) and trypsin (500 U/ml) (Sigma T-8642) in HBSS (with 1 mM $Ca^{2+}$, 1 mM $Mg^{2+}$, supplemented with 10 mM HEPES, pH 7.4, a 100 U/ml penicillin–100 μg/ml streptomycin solution, 100 μg/ml neomycin (Gibco 15310-014 or equivalent), 50 μg/ml gentamicin (Gibco 15710-015 or equivalent), and 0.625 μg/ml amphotericin B (Fungizone) (Gibco 15295-017 or equivalent). Two to four valves were incubated in a 400 or 600 ml container with 80 ml solution/valve, for a total of 160–320 ml of solution. The valves were incubated for 3 hours, at 37° C., with agitation on a shaking platform, 110 rpm.

6. The tissue was transferred to a 1.0 liter, screw capped vessel and washed with a solution consisting of HBSS, without $Ca^{2+}$ or $Mg^{2+}$, and with a 100 U/ml penicillin–100μ/ml streptomycin solution, 10 mM HEPES pH 7.4, 10 mM EDTA, 1 μM PMSF and 0.2 mM BHA, pH 7.4. Three to six valves were transferred into each container with wash solution, 90 ml/valve. The tissue was then washed for 15 min at room temperature, with agitation on a shaking platform at 110 rpm. The washing procedure was repeated for a total of three washes.

7. The solution was decanted and steps 3 to 6 were repeated.

8. At the end of the final washing procedure in step 7, the spent solution was decanted and the valves placed in a solution containing HBSS without $Ca^{2+}$ and $Mg^{2+}$, with 10 mM HEPES, pH 7.4, a 100 U/ml penicillin–100 μg/ml streptomycin solution, 0.1 mM BHA and 1 μM PMSF. The washing procedure was repeated for a total of three washes. The spent solution was decanted, fresh solution added and the tissue was stored at 4° C. until ready for use.

Soluble protein of the valves as prepared above was determined with a cold water extraction procedure. Cold water extractable protein contains globular intracellular proteins and so-called soluble collagen, the latter constituting a small percentage of the total valve "structural" proteins comprising collagen and elastin. The following methods, using standard organic chemistry methodologies, were used to determine soluble protein content of the leaflets.

Water loss on drying and dry weight were determined by (1) weighing the wet tissue, (2) drying in a 110° C. oven to a constant (dry) weight, and (3) subtracting dry weight from wet weight. Dry weight was used as the denominator for all other measurements. Percent water loss on drying allows conversion from wet weight to dry weight.

Freshly decellularized leaflets were frozen in liquid nitrogen and ground to a fine powder in a pre-chilled, pre-weighed mortar and pestle. The powder was transferred to a desiccator and allowed to thaw for 10–30 min. The mortar and ground valves were weighed, and the (wet) weight of the valve tissue determined by subtracting the weight of the mortar and pestle from the total weight.

Ground valves were quantitatively transferred to rinsed plastic centrifuge tubes using about 8 ml of water per gram of tissue. The mixture was homogenized on ice for 1 min. with an Ultra-Turrax homogenizer at 20,000 rpm. The homogenate was then centrifuged for 10 min. at room temperature at low speed (approximately 500×g) to pellet insoluble debris. The clear, pinkish supernatant was decanted into a volumetric flask. The pellet was subjected to another cycle of homogenization and centrifugation; the resulting supernatant was added to the first supernatant. The final pellet underwent a third cycle of homogenization and centrifugation, with all supernatants combined in the volumetric flask. The combined supernatants were brought to a reference volume with water (25 ml or 50 ml depending on the amount of starting material), aliquoted and frozen pending further analysis. The Lowry procedure was performed on the extract to determine protein content, using a commercially available kit (Sigma Diagnostics Protein Assay Kit, Cat. No. P5656).

The soluble protein content of the matrix produced from a porcine valve leaflet through the methods as set out above was 0.8% of the dry weight of the leaflet. In contrast, soluble protein accounted for 11.4% of the dry weight of an intact porcine valve leaflet.

EXAMPLE 2

Phospholipase Without Protease Protocol

At the slaughterhouse, adult pigs were sacrificed and the hearts were immediately removed and stored on ice until ready for use (about 4–8 hr later).

1. The aortic valve was removed from each heart and rinsed extensively in isotonic saline (0.9% NaCl in deionized, distilled water) supplemented with 1 μM PMSF and a 100 U/ml penicillin–100 μg/ml streptomycin solution. When used, PMSF is added to the solution just prior to use due to its limited activity.

2. The valves were transferred to a 1.0 liter, sterile, screw capped container and incubated in a hypotonic solution consisting of 10 mM TRIS, 5 mM EDTA, pH 8.0, supplemented with a 100 U/ml penicillin–100 μg/ml streptomycin solution, 0.1 mM BHA and 1 μM PMSF. The incubation period was for 22 hours, at 4° C., on a shaking platform, 110 rpm. Three to six valves were incubated in 270–540 ml of the solution (i.e., 90 ml/valve). The spent solution was exchanged with fresh solution 3 times during the incubation period.

3. At the end of the incubation period the solution was decanted and replaced with a hypertonic solution consisting of 50 mM TRIS, 10 mM EDTA, 1.0N NaCl, pH 8.0, supplemented with a 100 U/ml penicillin–100 μg/ml streptomycin solution, 0.1 mM BHA and 1 μM PMSF. The valves were incubated in this solution for 22 hours, at 4° C., on a shaking platform, 110 rpm. The spent solution was exchanged with fresh solution 3 times during the incubation period.

4. The valves were transferred to sterile 1.0 liter capped containers containing 90 ml/valve of HBSS with 1 mM $Ca^{2+}$, 1 mM $Mg^{2+}$ and 10 mM HEPES pH 7.4. The valves were washed for 15 minutes, at room temperature, on a shaking platform, 110 rpm. The solution was decanted, fresh solution added and the washing procedure repeated for a total of three 15-minute washes.

The last wash solution was decanted and the valves were then incubated for 30 minutes at 37° C. in a fourth volume of the same wash solution, on a shaking platform, 110 rpm.

5. The valves were transferred to a smaller, sterile, capped vessel containing a solution consisting of phospholipase $A_2$ (5 U/ml), phospholipase C (2.5 U/ml), phospholipase D (10 U/ml), DNase I (50 μg/ml) and RNase A (83.3 μg/ml) in HBSS (with 1 mM $Ca^{2+}$, $Mg^{2+}$, and 10 mM HEPES, pH 7.4) supplemented with 0.625 μg/ml amphotericin B, 50 μg/ml gentamicin, 100 μg/ml neomycin, and a 100 U/ml penicillin–100 μg/ml streptomycin solution. Two to four valves were incubated in a 400 or 600 ml container with 160–320 ml of solution, e.g. 80 ml per valve. The valves were incubated for 3 hr, at 37° C., with agitation on a shaking platform, 110 rpm.

6. At the end of the incubation period the valves were transferred to a 1.0 liter, sterile, screw capped container and washed for 15 minutes, at room temperature, on a shaking platform, 110 rpm, in HBSS without $Ca^{2+}$ or $Mg^{2+}$, with 10 mM HEPES, pH 7.4, 10 mM EDTA, supplemented with a 100 U/ml penicillin–100 μg/ml streptomycin solution, 0.2 mM BHA and 1 μM PMSF. Three to six valves were washed in 90 ml/valve of the solution, or 270–540 ml total. The solution was decanted, fresh solution was added and the washing repeated for a total of three washes.

7. The solution was decanted and steps 3 to 6 repeated.

8. Upon completion of the incubation period the solution was decanted and replaced with HBSS (without $Ca^{2+}$, $Mg^{2+}$, and with 10 mM HEPES, pH 7.4) supplemented with a 100 U/ml penicillin–100 μg/ml streptomycin solution, 0.1 mM BHA and 1 μM PMSF. The tissue was rinsed once with this solution and stored in the same solution at 4° C. until ready for use.

EXAMPLE 3

Cryopreservation

At the slaughterhouse, adult pigs were sacrificed and the hearts were immediately removed and stored on ice until ready for use (~4–8 hr later).

The aortic valve was removed from each heart and rinsed extensively in isotonic saline (0.9% NaCl in deionized, distilled water) supplemented with 1 μM PMSF, and a 100 U/ml penicillin–100 μg/ml streptomycin solution. PMSF was added to the solution just prior to use due to its limited activity. The valves were placed in a screw capped freezing vessel containing cryoprotectant and store at −20° C. until ready for use (three valves per about 50 ml solution). The cryoprotectant consisted of Dulbecco's Minimal Essential Medium (MEM), 10% dimethylsulfoxide (DMSO) and 10% fetal bovine serum (FBS).

At the time of cell removal, the frozen valves were quickly thawed in a 37° C. water bath, transferred to a 1.0 liter, sterile, screw capped container and incubated in a solution consisting of 10 mM TRIS, 5 mM EDTA, pH 8.0, supplemented with a 100 U/ml penicillin–100 μg/ml streptomycin solution, 100 μg/ml neomycin, 0.1 mM BHA and 1 μM PMSF. The incubation periods was for 72 h, at 4° C., on a shaking platform, 110 rpm. Three-six valves were incubated in 250–500 ml of the solution. The spent solution was exchanged with fresh solution 1–3 times during each 24 hr period of the incubation period.

The procedure was then continued as described in Example 2, above.

EXAMPLE 4

Recellularization

Human arterial endothelial cells (HAECs) from a 37-year-old male donor at passage 4 were obtained from Clonetics, San Diego, Calif. (Clonetics Cat. No. HCA CE 2793). HAEC were cultured and passaged as recommended, using media supplied by Clonetics. Cultures were grown to 80% confluence before experimental manipulations. When sufficient cells were obtained by expansion, cultures were harvested by trypsinization and resuspended in endothelial cell (EC) culture medium at $10^7$ cells/ml. The EC culture medium was obtained from Clonetics (Clonetics Cat. No. CC-3024) and consisted of MCDB131 medium, slightly modified from Knedler et al., In Vitro Cell and Develop. Biol. 23: 481–91.

Neonatal rat cardiac fibroblasts (NMC) were isolated and cultured as described in Bishopric et al., Proc. Natl. Acad. Sci. USA 88: 2132–36 (1991), and Webster et al., J. Biol. Chem. 268: 16852–59 (1993). Briefly, hearts from 30 to 40 pups were minced and subjected to serial trypsin digestion to release single cells. After the final digestion the cells were washed and plated for 30 minutes in MEM with 5% fetal bovine serum. The cells that attached during this step were approximately 95% fibroblasts and 5% smooth muscle cells as determined by actin staining. Cells were passaged once before use, which was sufficient to eliminate a relatively small number of contaminating cardiac myocytes. When sufficient cells were obtained by expansion, cultures were harvested by trypsinization and resuspended in MEM with 5% fetal bovine serum (FCS) at $10^7$ cells/ml.

Valve leaflets were prepared from fresh porcine aortic valves and subjected to decellularization by enzymatic digestion with the phospholipase mixture as described in Example 2, above. Additional leaflets were prepared using the phospholipase plus trypsin procedure as described in Example 1, above. All leaflets were sterilized after cell extraction by exposure to a total of 25 Kgray gamma irradiation from a cesium source. Following irradiation, leaflets were equilibrated with cell culture media by overnight incubation at 4° C. On the following day leaflets were transferred to individual 60 mm tissue culture dishes with fresh media, and incubated for an additional 24 hours at 37° C. in a humidified 5% $CO_2$ incubator.

At the end of leaflet pre-incubation, aliquots of cell suspensions containing $5 \times 10^6$ cells (either HAEC or NMC) were layered onto the upper surface of each leaflet. The cells and leaflets were transferred back into the incubator and the cells were allowed to attach without agitation overnight. On the following day media was changed and cell spreading and growth allowed to continue for an additional two to five days. Representative leaflets were examined at the level of the light and transmission electron microscope.

Figure 1:
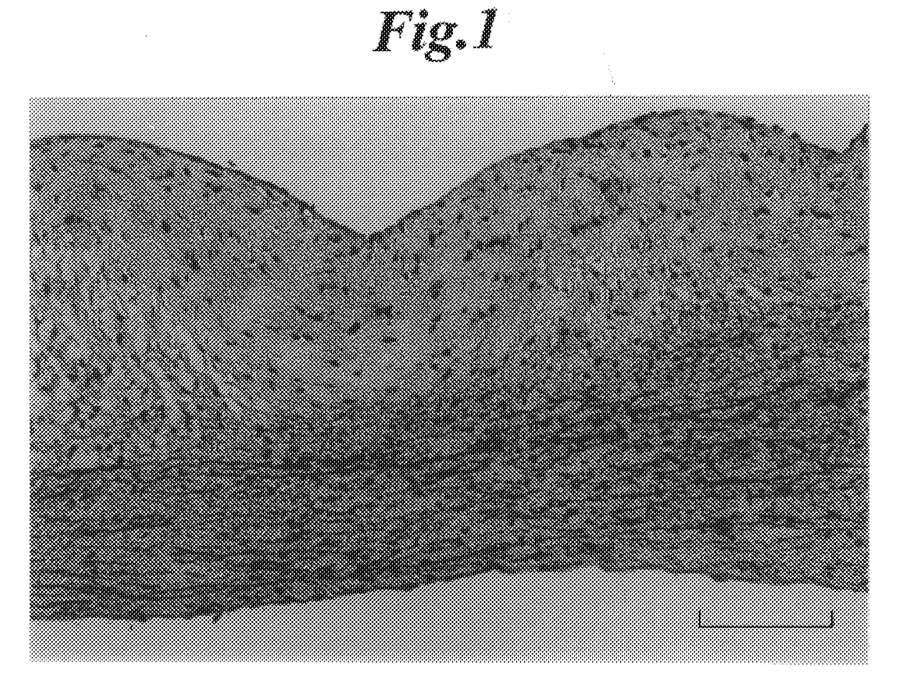
FIG. 1 is a light micrograph of a Movat Pentachrome-stained section of a normal, untreated porcine aortic valve leaflet. Bar=100 μm.

Results are shown in FIGS. 1–7. FIG. 1 shows a normal, untreated porcine aortic valve leaflet. Fresh tissue was harvested and immediately placed in Bouin's fixative, followed by embedding in paraffin and sectioning. The section shown in FIG. 1 was stained with Movat's pentachrome. In this black and white print, elastin and cell nuclei appear black and collagen fibers appear grey. Numerous cells (dark dots) can be observed evenly distributed throughout the thickness of the leaflet.

FIG. 2 shows a porcine aortic valve leaflet prepared from fresh aortic valves and subject to decellularization as described above in Example 2. Tissue was fixed in 4% paraformaldehyde. The tissue was then embedded in paraffin, sectioned and stained with Movat's pentachrome exactly as in FIG. 1. The surface and interior of the leaflet are substantially devoid of intact cells, and collagen and elastin remain abundant.

FIG. 3 shows a porcine valve leaflet prepared according to the methods of Example 2, above, fixed and stained with Verhoeff-Van Giesen stain. As with the Movat stain in FIGS. 1 and 2, cell nuclei and elastin are visible as black elements against the collagen-containing grey background. Elastin can be seen along the left margin of the tissue. FIG. 3 shows extensive decellularization of the fibrous annulus of the aortic root (R) adjacent to the region of insertion of the leaflet (L). Dark spots within the adjacent muscle shelf (M) represent remnants of cells.

Figure 4:
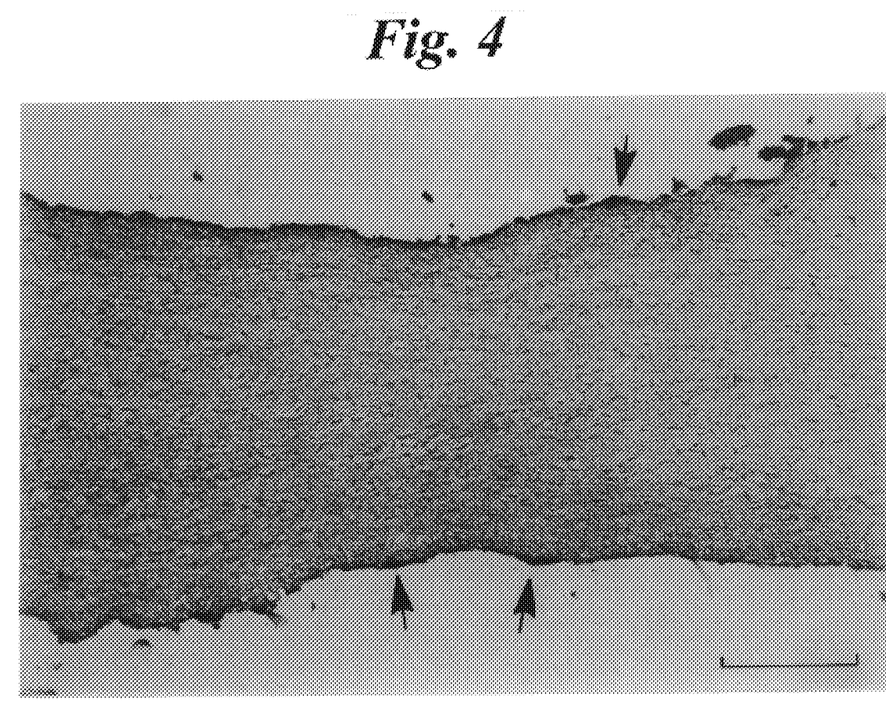
FIG. 4 is a light micrograph of a porcine aortic valve leaflet decellularized with a phospholipase-based process of the present invention and recellularized by incubation with human arterial endothelial cells for 2 days. Bar=100 μm.

FIG. 4 shows attachment of human arterial endothelial cells to valve leaflets extracted using the phospholipase-based method of Example 2. Human arterial endothelial cells were cultured as described above (Example 4) in the presence of a sterilized, decellularized porcine aortic valve leaflet for two days. The tissue was fixed, embedded in paraffin, sectioned, and stained with Gill's hematoxylin, which stains cell nuclei intensely. FIG. 4 clearly shows numerous dark-staining cell nuclei at the surface of the leaflet (arrows), indicating attachment of endothelial cells. Note the comparable appearance of cells on the surface of the normal valve leaflet (FIG. 1). This may be contrasted with the absence of cells on the surface of the leaflet shown in FIGS. 2 and 3.

Figure 5:
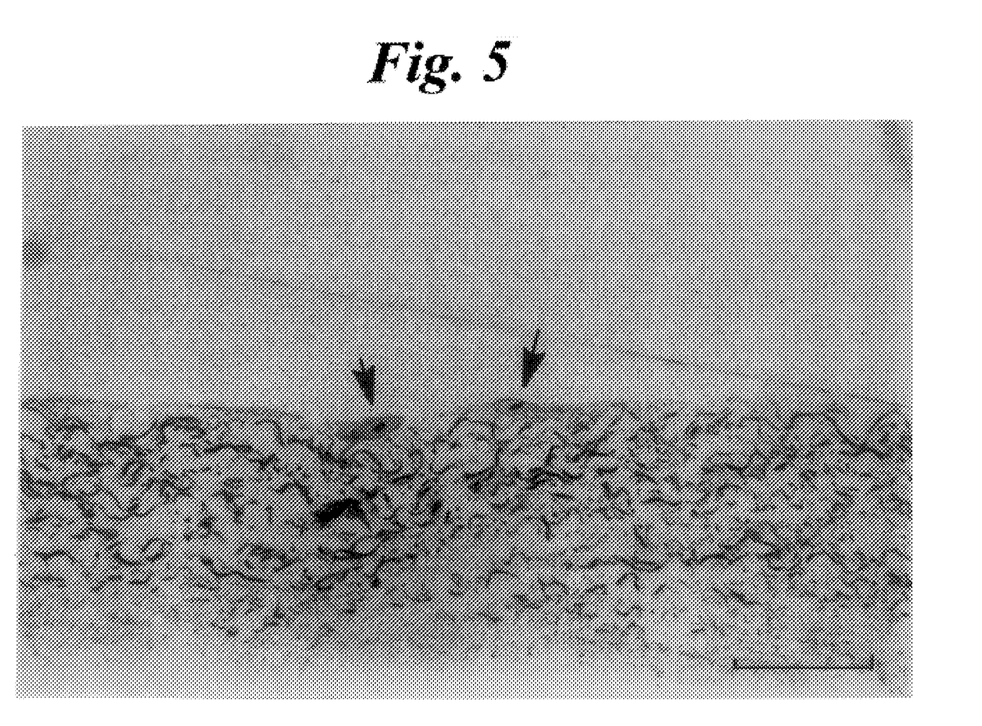
FIG. 5 is a higher magnification light micrograph of a 1 micron section of a leaflet processed as in FIG. 4, showing attached endothelial cells. Bar=50 µm.

See also FIG. 5, which is a higher-magnification view of a 1 micron plastic-embedded section of another leaflet prepared as in Example 2. The attachment of endothelial cells to the elastin- and collagen-containing matrix is apparent. Arrows in FIG. 5 indicate nuclei of attached endothelial cells.

Figure 6:
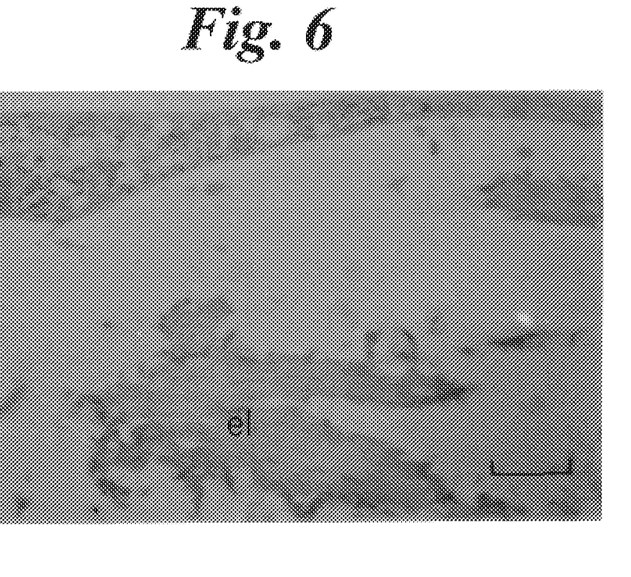
FIG. 6 is a transmission electron micrograph of a portion of a rat cardiac fibroblast seeded onto a porcine matrix as prepared in Example 1. Bar=1 µm.
Figure 7:
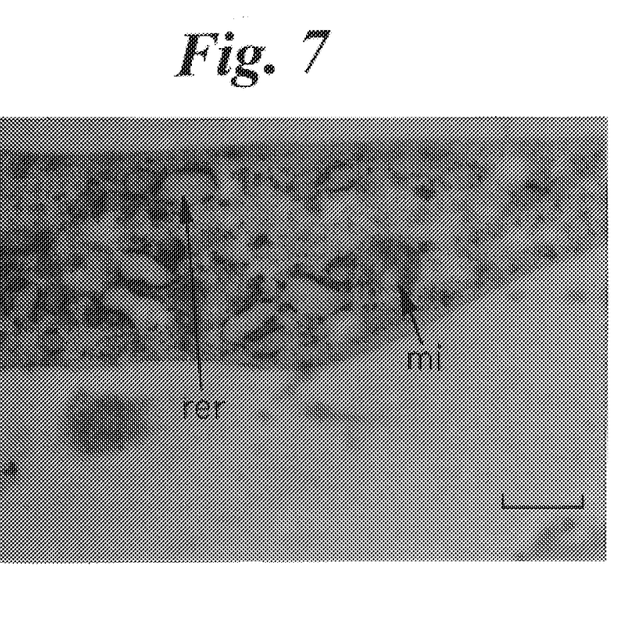
FIG. 7 is a transmission electron micrograph at higher magnification of a portion of the same fibroblast in FIG. 6, showing attachment and spreading. Bar=0.583 µm.

FIGS. 6 and 7 are electron micrographs of rat cardiac fibroblasts seeded onto leaflets decellularized according to the methods of the present invention. The micrographs demonstrate the ability of the seeded cells to attach and spread. Rat cardiac fibroblasts were cultured as described above (Example 4) and allowed to seed the surface of a sterilized, decellularized porcine aortic valve leaflet prepared as in Example 1, above. After 5 days the tissue was fixed and prepared for transmission electron microscopy.

FIG. 6 shows part of a fibroblast that has attached to and spread on the collagen- and elastin-containing (el) matrix. FIG. 7 shows the fibroblast of FIG. 6, at higher magnification. Note the presence of clusters of rough endoplasmic reticulum (rer) and mitochondria (mi), demonstrating the health and metabolic activity of the cell.

The results of the light and electron microscopy analyses demonstrate that rat cardiac fibroblasts and human arterial endothelial cells are capable of attaching and spreading on a vascular structure decellularized according to the methods of the present invention. The cells appear viable with ultrastructure indicative of an active cellular metabolism.

We claim:

1. A method of decellularizing a body tissue to form an extracellular matrix having substantially intact collagen and elastin components, said matrix being adapted for recellularization in vitro or in vivo, comprising subjecting said body tissue to incubation in a hypotonic solution followed by incubation in a hypertonic solution or incubation in a hypertonic solution followed by incubation in a hypotonic solution, then treating said body tissue with an enzyme-based solution comprising lipase and deoxyribonuclease.

2. The method of claim 1, wherein said body tissue is a vascular tissue.

3. The method of claim 2, wherein said vascular tissue comprises a heart valve.

4. The method of claim 1, wherein said enzyme-based solution further comprises protease.

5. The method of claim 4, wherein said protease comprises trypsin.

6. The method of claim 1, wherein said lipase comprises phospholipase.

7. The method of claim 6, wherein said phospholipase comprises one or more phospholipases selected from the group consisting of phospholipase $A_2$, phospholipase C, and phospholipase D.

8. The method of claim 1, wherein said enzyme-based solution further comprises ribonuclease.

9. The method of claim 6, wherein said enzyme-treated body tissue is rinsed and stored in a buffered salt solution lacking calcium and magnesium.

10. The method of claim 9, wherein said hypotonic/hypertonic treatment and said buffered salt solution include an antioxidant.

* * * * *